United States Patent [19]

Kaakinen

[11] Patent Number: 5,445,735
[45] Date of Patent: Aug. 29, 1995

[54] COMBINATION FILTER BLOCK AND EFFLUENT FLOW DEFLECTOR

[76] Inventor: John W. Kaakinen, 4131 N. Overlook Ter., Portland, Oreg. 97217

[21] Appl. No.: 376,020

[22] Filed: Jan. 19, 1995

Related U.S. Application Data

[63] Continuation-in-part of Ser. No. 200,827, Feb. 23, 1994, abandoned.

[51] Int. Cl.6 .............................................. B01D 35/00
[52] U.S. Cl. .................................... 210/247; 210/248; 210/436; 210/446; 210/455; 210/463; 422/101; 422/104
[58] Field of Search .............. 422/101, 102, 103, 104; 210/247, 248, 436, 446, 455, 463, 464, 472

[56] References Cited

U.S. PATENT DOCUMENTS

| | | | |
|---|---|---|---|
| 4,113,627 | 9/1978 | Leason | 210/446 |
| 4,361,483 | 11/1982 | Pall | 210/446 |
| 4,944,876 | 7/1990 | Miller | 210/446 |
| 5,061,450 | 10/1991 | Aoyagi | 422/102 |
| 5,139,951 | 8/1992 | Butz et al. | 422/102 |
| 5,253,514 | 10/1993 | Kaakinen | 73/61.73 |
| 5,283,038 | 2/1994 | Seymour | 422/102 |

Primary Examiner—Robert A. Dawson
Assistant Examiner—Robert James Popovics
Attorney, Agent, or Firm—Chernoff, Vilhauer, McClung & Stenzel

[57] ABSTRACT

There is disclosed a device for both holding a filter element and deflecting and draining filter effluent, which may be adapted to utilize one or more disposable filter cartridges. The device can be used in systems for performing analytical tests which include a filtration step, and is particularly useful in systems for measuring the fouling potential of water containing particulates.

3 Claims, 1 Drawing Sheet

COMBINATION FILTER BLOCK AND EFFLUENT FLOW DEFLECTOR

This is a continuation-in-part of application Ser. No. 08/200,827, filed Feb. 23, 1994, now abandoned.

BACKGROUND OF THE INVENTION

This invention relates to apparatus useful in performing analytical tests on liquid samples under pressure and more particularly to apparatus for supporting a filter membrane and intercepting filter effluent.

Apparatus for performing certain analytical tests on liquids, including the filter plugging or Silt Density Index (SDI) test for monitoring the particulate content of feed water to membrane water treatment processes such as reverse osmosis, typically includes a filter holder for supporting a filter membrane through which the pressurized test sample flows. Such apparatus typically requires connecting the filter holder to a sample outlet line as well as to the sample inlet line. When a fresh filter membrane is inserted into the apparatus of such a system, air tends to become entrained in the system. In such a system any air pockets or bubbles remaining after a purge will interfere with a subsequently performed analysis. In some apparatus the filter holder may not be connected to a sample outlet line, and filter effluent may be permitted to freely exit the filter holder outlet. In such a system the filter effluent may be merely discharged to a sink or similar drain, or it must be separately collected for alternate disposal. Discharging effluent to a drain tends to be messy because of uncontrolled splashing, while separately collecting the effluent is time consuming and inconvenient, particularly when many samples must be analyzed.

Further, in existing apparatus of the type described there is provision only for a single filter cartridge at a time, which requires manual replacement of the filter cartridge after each SDI test, as well as a shutdown of the testing apparatus while the spent filter cartridge is replaced.

Thus, there is still a need for apparatus for holding one or more filters which permits deflecting filter effluent, which is easy to purge of air or dispenses with the need to purge air after a filter change, and which permits an unattended sequence of SDI tests, and uninterrupted operation of SDI testing apparatus.

SUMMARY OF THE INVENTION

The present invention comprises a device for both holding a filter element and deflecting and draining pressurized filter effluent, and may be adapted to utilize a disposable filter cartridge.

The device can be used in systems for performing analytical tests which include a filtration step, and is particularly useful in systems for measuring the fouling potential of water containing particulates such as is disclosed in U.S. Pat. No. 5,253,514, the disclosure of which is incorporated herein by reference.

DETAILED DESCRIPTION OF THE INVENTION

Figure 1:
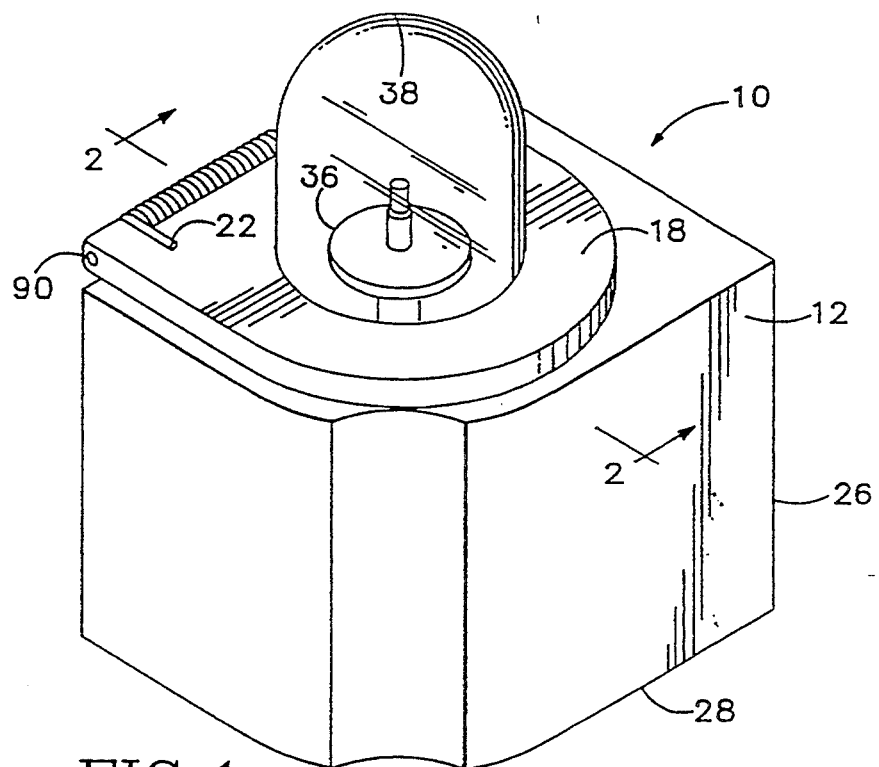
FIG. 1 is a perspective view of an exemplary filter block and effluent deflector embodying the present invention.
Figure 2:
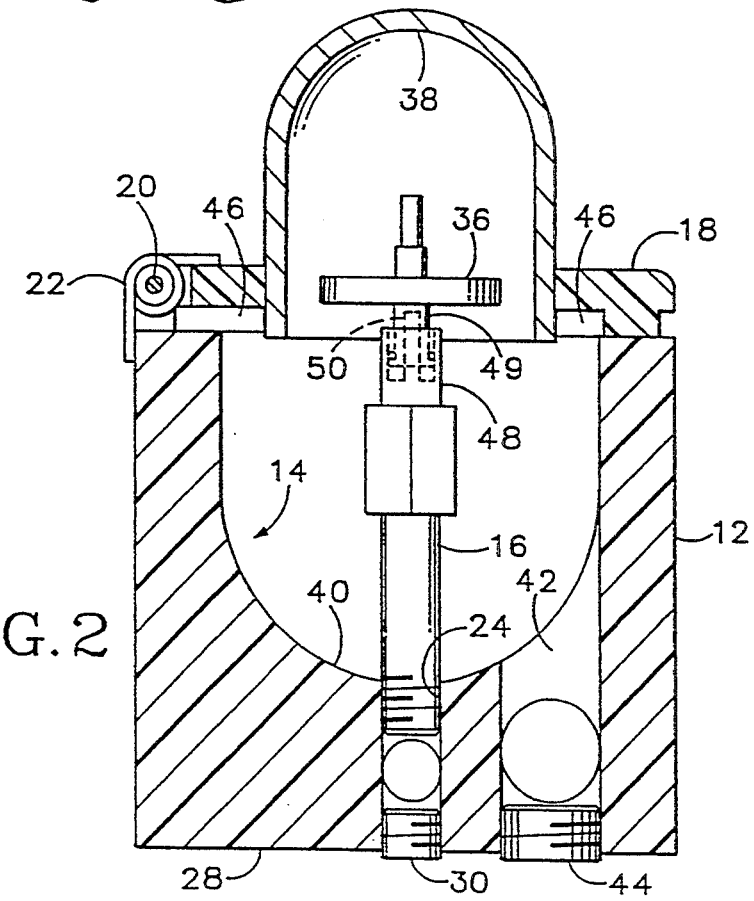
FIG. 2 is an enlarged sectional view taken along line 2—2 of FIG. 1.

Referring now to an exemplary embodiment of the invention illustrated in the drawings, a filter block 10 includes a housing 12 defining an interior 14 within which filter holder 16 is located. The housing 12 has attached thereto a cover 18 which provides access to the interior 14 and filter holder 16. The cover 18 may be completely detachable from the rest of the housing, or it may be hingedly attached by hinge 20 as shown. The hinge 20 may include a spring 22 or a similar biasing element for urging the cover to a closed position.

An inlet such as inlet conduit 24 communicates with the interior 14 of the housing 12. The inlet conduit may enter from a side 26, from the bottom 28, or from both the side and bottom of the housing, with a threaded removable stopper 30, stoppering the redundant conduit. The filter holder 16 is in fluid communication with the inlet conduit 24 for receiving pressurized liquid effluent. Given such an arrangement, prior to running an SDI test, one may simply flush effluent or water through inlet conduit 24 and filter holder 16 until it exits at the terminus 50 of the filter holder 16, thereby forcing out any air in the filter block assembly so as to prevent interference with an SDI test.

The filter holder 16 has an outlet 48 which has a male portion 50 which is adapted to matingly receive female portion 49 of filter cartridge 36. A portion of the interior surface of the cover 18, located generally opposite the filter holder outlet 48, defines an effluent deflector 38 which is located to deflect filtered effluent or filtrate. The effluent deflector 38 may be defined by the interior surface of a dome-shaped portion of the cover 18, and may be made of a transparent material such as glass or a transparent polymeric material which permits visual observation of the filter holder and the interior of the housing during operation of the apparatus. Preferably, the effluent deflector 38 is located sufficiently far away from the top opening of filter cartridge 36 so as to not cause any substantial increase above atmospheric pressure on the filtrate side of filter cartridge 36 due to filtrate flow impinging on effluent deflector 38.

The filter holder 16 is adapted to receive and support filter cartridge 36. In a preferred embodiment, the filter holder outlet 48 is equipped with Luer-Lok ®-type threads extending radially inwardly from the base of filter holder outlet 48, which may be matingly and frictionally engaged by corresponding female Luer-Lok ® projecting tabs at the base of filter cartridge 36 which contains a filter element, allowing rapid and secure connection and disconnection of the filter cartridge 36 to the filter holder 16. In a preferred embodiment, a disposable filter cartridge 36 comprising a housing enclosing a filter element such as the Millex HA filter module sold by Millipore Corporation of Bedford, Mass., containing a cellulose acetate filter membrane, is secured to the filter holder 16 by Luer-Lok ® connector elements, so as to resist the pressure of the pressurized liquid effluent, and thereby maintain the filter cartridge and filter element in fluid communication with the effluent inlet by way of mating engagement with filter holder outlet 48.

A basin 40 is located within the housing 12 for receiving effluent and filtrate deflected by the effluent deflector 38. An outlet such as an outlet conduit 42 communicates with the interior of the housing and basin 40. The outlet conduit may exit the housing from the side 26, from the bottom 28, or both from the side and the bottom of the housing as shown, with a threaded removable stopper 44 stoppering the redundant conduit.

In a preferred embodiment of the present invention there is a gap between the housing 12 and the cover 18 which defines a vent 46 for insuring that the pressure in the interior of the housing 12 is at essentially atmospheric pressure.

Though not depicted in the drawings, it is within the contemplation of the present invention to provide multiple inlet conduits 24, each being in fluid communication with multiple corresponding filter holders 16, with each filter holder 16 in turn being adapted to receive and support a filter cartridge 36. Each of the multiple inlet conduits 24 would either be in fluid communication with the source of effluent or be capable of being placed in fluid communication therewith by valve means, either sequentially or in any other order. The valve means could be operated remotely by solenoid switching means.

In operation, the apparatus is connected to a system requiring a filter holder for performing an analytical test having a filtering step, and it is particularly useful in systems for measuring water-borne particulates wherein the same are in an effluent that is under an applied pressure greater than atmospheric pressure. The inlet conduit 24 is attached to a system such as the plugging factor analyzer disclosed in U.S. Pat. No. 5,253,514, serving as the filter means. Prior to the initial SDI test, cover 18 is closed and air is purged by permitting pressurized water or effluent to be tested to flow through the filter block inlet conduit 24 out through the terminus 50 of filter holder 16. (Subsequent tests may be run without such an air purge as long as water or effluent remains visible in terminus 50.) The cover 18 of the housing 12 is opened and a filter cartridge 36 containing a filter element is connected to the filter holder 16. The cover 18 may include a magnet that aligns with a magnetic force sensor (not shown) in the filter block 10, the sensor detecting the proximity of the magnet, thereby providing information as to whether the cover is open or closed.

After the cover is closed, the analytical test is initiated. The inlet conduit 24 is filled with liquid effluent, which may be pressurized by means of a pump, for example, to a pressure greater than atmospheric pressure. The pump may be used to insure that the inlet conduit 24, filter holder 16 and connector 34a are full of liquid prior to removing the used filter membrane, installing a fresh filter membrane and initiating a test, or a valve (not shown) may be included upstream of the filter holder for that purpose. In a preferred embodiment, the membrane filter is oriented upright relative to the gravitational pull of the earth, and perpendicular to the liquid effluent stream to facilitate removal of air from the system and to keep the filter holder 16 full of water up to terminus 50.

With the cover in the closed position, liquid is forced through the filter element and liquid effluent exits the filter cartridge 36 to be deflected by the effluent deflector 38. Because of the vent 46, the interior 14 of the housing 12, including the basin 40, is at essentially atmospheric pressure, and the effluent deflected by effluent deflector 38 is collected in the basin 40 or is removed from the basin through outlet conduit 42. At the conclusion of the filtration, the cover 18 may be opened, the used filter cartridge quickly and easily removed and a new one installed, and the cover 18 closed prior to the initiation of the next filtration sequence.

The terms and expressions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A combination particulate filter holder and pressurized effluent flow deflector comprising:
    (a) a housing;
    (b) at least one effluent inlet in said housing constructed and arranged for receiving a particulate-containing liquid effluent that is under pressure;
    (c) at least one filter holder constructed and arranged to withstand the pressure of pressurized liquid effluent and having an inlet and an outlet, said inlet and said outlet being in fluid communication with said at least one effluent inlet and constructed and arranged to hold at least one particulate filtering means;
    (d) at least one particulate filtering means constructed and arranged to withstand the pressure of pressurized liquid effluent;
    (e) a filtrate flow deflector for deflecting filtrate that has passed through said at least one particulate filtering means, said filtrate flow deflector substantially surrounding the outlet of said at least one filter holder;
    (f) a basin in said housing for receiving filtrate from the outlet of said at least one particulate filtering means and filtrate deflected by said filtrate flow deflector; and
    (g) an outlet in said housing in fluid communication with said basin.

2. The apparatus of claim 1 wherein said at least one filtering means comprises a disposable filter cartridge having a filter element.

3. The apparatus of claim 1, including a vent for maintaining the interior of said housing at essentially atmospheric pressure.

* * * * *